United States Patent [19]

Oxenrider

[11] 4,252,982
[45] Feb. 24, 1981

[54] ALIPHATIC ESTER SOLVENT IN ESTERIFICATION OF CARBOXYBENZENES

[75] Inventor: Bryce C. Oxenrider, Florham Park, N.J.

[73] Assignee: Allied Chemical Corporation, Morris Township, Morris County, N.J.

[21] Appl. No.: 88,989

[22] Filed: Oct. 29, 1979

[51] Int. Cl.$^3$ .............................................. C07C 67/08
[52] U.S. Cl. ......................................... 560/87; 560/84
[58] Field of Search .............................. 560/87, 98, 84

[56] References Cited

U.S. PATENT DOCUMENTS

| | | | |
|---|---|---|---|
| 2,873,292 | 2/1959 | Meyer | 560/87 |
| 3,547,861 | 12/1970 | Anello et al. | 560/98 |
| 3,639,451 | 2/1972 | Ebert | 560/98 |
| 3,832,375 | 8/1974 | Itoh | 560/87 |

FOREIGN PATENT DOCUMENTS 1543031  3/1979  United Kingdom ...................... 560/87

*Primary Examiner*—James H. Reamer
*Attorney, Agent, or Firm*—Alan M. Doernberg; Robert A. Harman

[57] ABSTRACT

An anhydride of a carboxybenzene is esterified in solution by a fluorinated alcohol, using an aliphatic ester having a boiling point between about 50° C. and about 150° C. as solvent. In particular, pyromellitic dianhydride is esterified in an ester such as ethyl acetate or butyl acetate to the diester/diacid by reaction with 2-(n-perfluoroalkyl)ethanols having six to twelve carbon atoms in the perfluoroalkyl groups, and the reaction mixture containing the dissolved diester/diacid is admixed with an oxirane compound of the group ethylene oxide, epichlorohydrin and glycidol whereby the carboxyl groups are esterified in the solvent by reaction with oxirane groups. The product is recovered by evaporating off the solvent and unreacted oxirane compound. The product imparts oil and/or water repellency to textiles.

9 Claims, No Drawings

ALIPHATIC ESTER SOLVENT IN ESTERIFICATION OF CARBOXYBENZENES

DESCRIPTION

Background of the Invention

This invention relates to esterification of carboxybenzenes, especially such esterification in solution by contact of an anhydride of a carboxybenzene with a fluorinated alcohol. Such esterification process is broadly known, and is especially useful in preparation of compounds capable of imparting oil and/or water repellency to textiles, especially to fibers of PET and nylon.

In particular, as disclosed in British Pat. No. 1,543,081 to my assignee, published Mar. 28, 1979, very useful agents for imparting oil and water repellency are obtained by contacting in solution an anhydride of a carboxybenzene especially pyromellitic dianhydride and various fluorinated alcohols to form the corresponding fluorinated ester/acid and by then contacting in solution the resulting fluorinated ester/acids with an oxirane compound of the group ethylene oxide, epichlorohydrin, or glycidol. Thus, specifically, pyromellitic dianhydride ("PMDA") is esterified in Example 5 Part G of BP No. 1,543,081 by a mixed perfluoro-n-hexyl-, perfluoro-n-octyl-, or perfluoro-n-decylethanol in dry dimethylformamide ("DMF") solvent; the resulting diester/diacid is isolated; and the diester/diacid is admixed with epichlorohydrin in dry acetonitrile using a little pyridine as catalyst to bring about an esterification reaction of the carboxyl groups of the diester/diacids with the oxirane group of epichlorohydrin. The product is precipitated out with ice water.

More generally, esterification of anhydride by fluorinated alcohol has been disclosed using solvents such as benzene, pyridine, quinoline, nitrobenzene, dimethylaniline, Decalin and 1,1,2-trifluoro-1,2,2-trichloroethane; in particular for anhydrides of acrylic compounds—U.S. Pat. No. 3,547,861 of Dec. 15, 1970 to Anello et al. at column 4, lines 1–41.

In copending U.S. patent application Ser. No. 44,880 of Bryce C. Oxenrider and Frank Mares filed June 4; 1979, such esterifications are disclosed with N-methylpyrrolidone ("NMP") are disclosed. In the examples, a mixture of 2-(n-perfluoroalkyl)ethanols was reacted in NMP (and in DMF in a comparison) to form the diester/diacid in solution and then epichlorohydrin and an organic base were added to bring about an esterification reaction of the carboxyl groups of the diester/diacid with the oxirane groups of epichlorohydrin. The product was then precipitated out by stirring in excess water, washing with water and drying under vacuum.

While DMF and NMP are excellent solvents for the desired esterification reaction, they offer certain handling and recovery problems. First DMF has a recognized toxic level of >10 ppm and therefore release of DMF must be carefully controlled during the process. NMP is substantially non-toxic, but evidence has been presented of its terotagenic activity, and thus release of NMP must also be carefully controlled during the process. Furthermore, since DMF and NMP have relatively high boiling points of 152.8° C. and 202° C., respectively, they cannot conveniently be separated from the intermediate or first reaction product by distillation. The expedient employed in British Pat. No. 1,543,081 and copending application Ser. No. 44,880 of drowning the product mixture in water causes the solvent to be dissolved in waste water and thus a potential environmental concern because of the toxicity of DMF and the terotagenic activity of NMP. Failure to remove DMF or NMP from the product below levels such as about 0.25 weight % may render the product unsuitable for many fiber uses because of the same toxicity of DMF and terotagenic activity of NMP.

When DMF or NMP are used in solvents for a two-step process of first esterification to an ester/acid and then epoxidation, particularly with epichlorohydrin, the inability to easily distill the solvent from the product mixture has additional disadvantages. Since epichlorohydrin may be employed in excess in order to drive the epoxidation reaction to completion in a reasonable time, unreacted epichlorohydrin is usually present in the product mixture. The presence of epichlorohydrin in the waste water could present an environmental concern; presence of epichlorohydrin in the product will limit its applications.

BRIEF DESCRIPTION OF THE INVENTION

The present invention employs aliphatic esters having a boiling point of between about 50° C. and about 150° C. as the solvent for the esterification of a carboxybenzene by contact of an anhydride of such carboxybenzene with a fluorinated alcohol. These esters can be distilled from the direct product of this esterification or from the further product of epoxidation of an ester/acid product of the esterification with an oxirane compound selected from epichlorohydrin, ethylene oxide and glycidol. Epichlorohydrin or ethylene oxide can then be removed in the vapor phase with the solvent for recycling. Since these aliphatic esters have minimal toxicity and no recognized terotagenicity, the present invention eliminates the potential environmental and product safety concerns posed by the use of DMF and NMP as solvents.

Accordingly, the present invention includes an improvement in a process for the esterification in solution of a carboxybenzene with a fluorinated alcohol. In the improvement the solvent consists essentially of at least one aliphatic ester having a boiling point between about 50° C. and about 150° C.

DETAILED DESCRIPTION

Anhydrides of carboxybenzenes believed to be useful in the present process, in addition to pyromellitic dianhydride, are anhydrides of hemimellitic acid and trimellitic acid; those from other tetracarboxybenzenes including prehnitic acid and mellophanic acid; those of the pentacarboxybenzenes; and those of mellitic acid.

Numerous fluorinated alcohols are disclosed in the prior art, for example in BP No. 1,543,081 and U.S. Pat. No. 3,547,861 above cited, all of which alcohols are believed to be operative in the present process. These include fluorinated alcohols having straight chain, branched chain and cyclic fluorinated moities attached to a hydroxy substituted hydrocarbon moiety, each moiety having between 2 and 20 carbon atoms, especially such alcohols in which the fluorinated moiety has between 3 and 12 carbon atoms and the hydrocarbon moiety has between 2 and 12 carbon atoms. The fluorinated moiety can be perfluorinated and can alternatively be partially fluorinated, for example having a terminal hydrogen atom. Also either or both the fluorinated moiety and the hydroxyl substituted moiety can contain substituents such as chloro, bromo or iodo; and the same applies to the coreactant, the anhydride of a carboxybenzene.

Specific suitable fluorinated alcohols for esterification of carboxybenzenes by the present process include the (perfluoroalkyl)ethanols and the (perfluoroalkyl)propanols having three to twelve carbon atoms in the perfluoroalkyl groups; and the (omega-perfluoroisopropoxyperfluoroalkyl)ethanols, and the propanol homologues thereof, having two to ten carbon atoms in the perfluoroalkyl groups. Preferred alcohols of the above group, in view of their availability and effectiveness in producing esters with the desired properties, are mixtures consisting essentially of 2-(n-perfluoroalkyl)ethanols having six to twelve carbon atoms in the perfluoroalkyl groups. Temperature and pressure used for the reaction are not critical and will be chosen to give a satisfactory reaction rate while avoiding decomposition of the products such as decomposition due to thermal rearrangement.

A catalyst is not necessary in the reaction of the fluorinated alcohol with the anhydride but conventional catalysts for this reaction such as bases or Lewis acids can be used if desired. A catalyst is helpful in the epoxidation reaction of the oxirane compound with the carboxyl group of the ester/acid with an organic base such as triethylamine or other trialkylamines being especially preferred.

The solvent must be selected for low toxicity, suitable boiling point and inertness to reaction with the reactants under conditions suitable for the desired esterification or esterification and epoxidation. The solvent must, of course, dissolve the carboxybenzene reactant and the product of esterification (an ester or ester/acid) sufficiently for the desired reaction to occur within a reasonable time to be a "solvent" within the meaning herein used. High solubilities are not required, however, since a portion of the carboxybenzene may remain undissolved while another portion in solution reacts so that more carboxybenzene may then dissolve.

Certain aliphatic esters have been found to meet these criteria for the preferred reaction between certain fluorinated alcohols and PMDA. It is believed that these aliphatic esters will also meet these conditions for esterification reactions within the broad scope of the present invention. Suitable esters include esters of formic, acetic, propanoic (propionic), butanoic (butyric) and pentanoic (valeric) acids having boiling points between about 50° C. and about 150° C. such as propyl formate, methyl acetate, ethyl acetate, propyl acetate, isobutyl acetate, butyl acetate, pentyl acetate, methyl propionate, ethyl propionate, butyl propionate, methyl butyrate, ethyl butyrate and methyl valerate. Especially preferred are the acetate esters such as ethyl, propyl and butyl acetates.

The use of the present esters as solvents overcomes the problems associated with DMF and NMP without incurring substantial additional difficulties. For many esterifications and subsequent epoxidations, the reaction rate may be slower in the present esters than in DMF or NMP (as is the case in the epoxidation reaction shown in the Examples), but the reaction does not become uneconomically slow and can be speeded up with appropriate catalysts. The present esters also may present flammibility hazards not present with DMF or NMP, but such problems can be overcome by using non-sparking equipment where the solvent is close to its flash point.

EXAMPLE 1

A 100 mL 3-neck flask (glass) fitted with stirring bar, thermometer, water condenser and inlet tube for nitrogen gas was oven dried and cooled in a desiccator. This flask was then charged with 16.5 g (about 0.036 mol) of a mixture of 2-(n-perfluoroalkyl)ethanols having six to twelve carbon atoms in the perfluoroalkyl groups, 3.97 g (0.0182 mol) of PMDA and 16.8 mL (15.0 g) of ethyl acetate. The flask was then immersed in a heated bath at 45° C. with stirring and a slow stream of nitrogen was passed through the flask to maintain a dry atmosphere, with care taken not to evaporate off excessive amounts of solvent by too much nitrogen flow. After several days the flask contained a milky white liquid, thick around the edges with a small stirred liquid pool in the middle.

8.55 mL (10.1 g) of epichlorohydrin and 0.15 mL (0.11 g) triethylamine (3 mole percent based on carboxyl groups) were added and the bath was raised to 60° C. About eight hours later the liquid was milky white with heavy solids indicating incomplete solubility. Some 24 hours from epichlorohydrin addition, the mixture had become a clear yellow solution with some gels still undissolved.

The solution was cooled to room temperature and poured into 800 mL of stirred cold water surrounded by an ice bath. After 30 minutes stirring, the liquid was decanted off and the precipitate washed three times with cold water. The washed solid was filtered and then vacuum dried at room temperature to yield 16.6 g of white tacky solids.

An aliquot was analyzed by NMR spectral analysis and the resonances closely matched those found for the product of Example 5 of British Pat. No. 1,543,081 including a triplet aromatic pattern and a $CH_2Cl$ doublet. The area integrations were consistent with those expected for the target composition.

Using the procedure of Example 10 of British Pat. No. 1,543,081 the products were applied to nylon-6 cloth at a level of 0.13% fluorine by weight of fibers which were annealed at 140° C. and at 155° C. and tested for resistance of oil repellency to laundering. While it is realized that laundering is not an exacting test method, the retention of oil repellency during laundering is an indication of the stability of the fluorocarbon surface on the nylon fiber. An arbitrary goal of oil repellency five after five laundry cycles was established as an indication of desirable stability even though fibers exhibiting a lower laundry stability than that can be utilized in some applications. When this product is compared with products prepared in NMP, the performance of the latter falls within the range exhibited in Table 1, below.

The oil repellency results for six cycles of washing and drying in a first run were:

| Cycles | 140° C. | 155° C. |
| --- | --- | --- |
| 0 | 7 | 7 |
| 1 | 7 | 6 |
| 2 | 6 | 6 |
| 3 | 5 | 5 |
| 4 | 4 | 4 |
| 5 | 1 | 3 |
| 6 | — | 2 |

A value of 5 or better after 5 cycles is considered acceptable, but as indicated above, the foregoing values are satisfactory for many uses. Additional nylon-6 samples were prepared, applying the products at the indicated levels of fluorine by weight of fibers and annealing at 140° C. and 155° C. The oil repellancy was as indicated in Table 1.

TABLE 1

| Solvent for Preparation | NMP | NMP | NMP | NMP | Ethyl Acetate | |
|---|---|---|---|---|---|---|
| Fluorine Applied | 0.10% | 0.10% | 0.15–0.19% | 0.15–0.19% | 0.15–0.17% | 0.15–0.17% |
| Annealing Temperature | 140° C. | 155° C. | 140° C. | 155° C. | 140° C. | 155° C. |
| 0 cycles | 8- | 8- | 8- | 8- | 7 | 7 |
| 1 | 7 | 7 | 7 | 7 | 7 | 7 |
| 2 | 7 | 7 | 7 | 7 | 6 | 6 |
| 3 | 6 | 7 | 6 | 6 | 6 | 6 |
| 4 | 6 | 6 | 6 | 6 | 6- | 6 |
| 5 | 3 | 6 | 5 | 5 | 4 | 4 |
| 6 | 2 | 6 | 4 | 4 | 2 | 4 |
| 7 | | 5 | 1 | 4 | | 4 |
| 8 | | 4 | | 1 | | 2 |
| 9 | | 4 | | | | |
| 10 | | 2 | | | | |
| 11 | | | | | | |

Using a fresh solution of material prepared substantially as in Example 1 using NMP as a solvent, the results of laundering nylon-6 swatches treated at a 0.15–0.17% fluorine level were:

| Cycles | 0 | 1 | 2 | 3 | 4 | 5 | 6 | 7 | 8 | 9 | 10 | 11 |
|---|---|---|---|---|---|---|---|---|---|---|---|---|
| 140° F. | 8- | 7 | 7 | 6 | 6 | 5 | 5 | 5 | 4 | 2 | | |
| 155° F. | 7 | 7 | 7 | 6 | 6 | 6 | 5 | 5 | 5 | 4 | 4 | 2 |

Thus, at similar levels of 0.15–0.19% applied agent, polymers prepared with ethyl acetate as solvent "passed" but did not perform quite as well as some of those prepared using NMP as solvent.

EXAMPLE 2

Example 1 was repeated using 23.9 g (0.052 30 mol) of fluorinated alcohols, 5.71 g (0.026 mol) of PMDA and 24.6 mL of ethyl acetate. After about 25 hours at 45° C., 0.22 mL (0.159 g or 0.00304 mol) of triethylamine and 12.28 mL (14.52 g or 0.278 mol) of epichlorohydrin were added.

After 16 hours at 60° C. the batch was split into portions A and B. A (37.5 g) was placed on a rotary flash evaporator at 60° C. in a 250 mL round bottom flask and vacuum dried at 100 mm mercury pressure (133 kPa). The temperature was slowly increased to 100° C. so that most of the solvent had evaporated off. The pressure was then lowered to 5 mm mercury (0.67 kPa) and, within 30 minutes evaporation appeared to have been completed. After 30 more minutes at 5 mm and 100° C. the brown, glassy product was weighed and found to be 19.9 g. Portion B was worked up in cold water as in Example 1 and yielded 10.3 g of beige tacky solids.

Both materials showed excellent correspondence by NMR to the product of Example 10 of British Pat. No. 1,543,081, Sample A showed no methyl impurity; sample B showed some methyl impurity suspected to be triethylamine.

Samples of A and B were applied to fibers at levels of 0.14% to 0.16% and annealed at 140° C. and 150° C. as indicated in Table 2. The repellency results after laundering the indicated number of cycles are displayed in Table 2.

TABLE 2

| Sample | A | A | B | B |
|---|---|---|---|---|
| Annealing Temp. | 140° C. | 155° C. | 140° C. | 155° C. |
| % F | 0.14–0.16% | 0.14–0.16% | 0.16% | 0.16% |
| 0 Cycles | 7 | 7 | 7 | 7 |
| 1 | 7 | 7- | 7 | 7 |
| 2 | 7- | 6 | 6 | 6 |
| 3 | 6 | 6 | 6 | 6 |
| 4 | 5 | 5 | 5 | 6 |
| 5 | 4 | 4 | 3 | 4 |
| 6 | 2 | 4 | 2 | 4 |
| 7 | | 4 | | 4 |
| 8 | | 3 | | 4 |
| 9 | | 2 | | 4 |
| 10 | | | | 2 |

EXAMPLE 3

Example 1 was repeated using 20.2 g (0.0442 mol) of fluorinated alcohols, 4.82 g (0.0221 mol) of PMDA and about 19 mL (42.0 g) butyl acetate. After about six and three-quarter hours at 45° C., 10.38 mL (12.28 g or 0.278 mol) of epichlorohydrin and 0.18 mL (0.134 g or 0.00304 mol) of triethylamine were added to the milky white liquid and the temperature was raised to 60° C. After about an hour, the liquid cleared. About sixteen and one-half hours after epichlorohydrin addition the liquid (53.9 g) was poured into a 250 mL single neck flask which was placed in a 60° C. bath. The pressure was dropped to 35 mm of mercury (4.67 kPa) when flashing began smoothly, without bumping. The temperature was raised slowly to 90° C., causing most of the solvent to be removed, then the pressure was lowered to 5 mm of mercury (0.67 kPa) and then the bath temperature raised to 125° C. and maintained for 30 minutes. After cooldown, 28.9 g of soft solids were recovered, and the structure confirmed by NMR which compared favorably with previous runs and with material prepared as in Example 5 of British Pat. No. 1,543,081. The results of laundering trials with this material, using the same procedures as in Example 1, are shown in Table 3.

TABLE 3

| Annealing Temperature | 140° C. | 155° C. | 140° C. | 155° C. |
|---|---|---|---|---|
| % F | 0.11–0.12% | 0.11–0.12% | 0.15% | 0.15% |
| 0 cycles | 6 | 7 | 7 | 7 |
| 1 | 6 | 7 | 7 | 7 |
| 2 | 6 | 6 | 6 | 6 |
| 3 | 6- | 6 | 6 | 6 |
| 4 | 5 | 5 | 6 | 6 |
| 5 | 5 | 5 | 6 | 6 |
| 6 | 4 | 4 | 4 | 5 |
| 7 | 4 | 4 | 4 | 5 |
| 8 | 4 | 4 | 2 | 5 |
| 9 | 3- | 2 | 1 | 5 |
| 10 | 1 | 1 | | 4 |
| 11 | | | | 3 |
| 12 | | | | 1 |

EXAMPLE 4

Example 1 was repeated using a 100 mL 3 necked flask with the same fittings and charging 28.5 g (0.061 mol) fluorinated alcohols, 6.68 g (0.0306 mol) PMDA and about 28 mL of butyl acetate to bring the weight of mixture to 58.9 g. After about 23 hours at 45° C., 14.4 mL (17.0 g or 0.278 mol) of epichlorohydrin and 0.26 mL (0.186 g or 0.003 mol) of triethylamine were added to bring the weight to 76.1 g. Raising the temperature to 60° C. cleared the milky white solution. The free epoxide was monitored by titrating a sample with glacial acetic acid (with HBr present) and, based upon the equivalents of PMDA used initially, the epoxide equivalents converted were 29.1% after two hours, 58.6% after 5 hours, 77.4% after 7.5 hours, 88.0% after 10.5 hours, 98.9% after 15.5 hours and 102.9% after 20.15 hours. 103% is the theoretical endpoint since 3% triethylamine is present by equivalents of PMDA. The flask was then sealed and stored overnight in a refrigerator.

The liquid (203.7 g) was then transferred to a 250 mL single necked flask and dried by successive temperature and pressure changes to 60° C., then to 100 mm of mercury (133 kPa), then slowly to 124° C., then slowly to 1.5 mm of mercury (0.2 kPa). After about 5 hours there and then cooldown, 35.9 g of an amber tacky solid with some drops of liquid on the surface were recovered. Gas chromatography showed about 3 ppm of a fluorinated alcohol with the other analyses showing fairly pure product. The results of laundering tests are displayed in Table 4.

TABLE 4

| Annealing Temperature | 140° C. | 155° C. |
|---|---|---|
| % F | 0.19 | 0.19 |
| 0 cycles | 7 | 7 |
| 1 | 7 | 7 |
| 2 | 6 | 6 |
| 3 | 6 | 6 |
| 4 | 6 | 6 |
| 5 | 6 | 5 |
| 6 | 4 | 4 |
| 7 | 3 | 4 |
| 8 | 1 | 2 |

What is claimed is:

1. In a process for esterification in solution of a carboxybenzene by contact of an anhydride of said carboxybenzene with a fluorinated alcohol; the improvement which comprises using a solvent consisting essentially of at least one saturated aliphatic ester having a boiling point between about 50° C. and about 150° C.

2. Process of claim 1 wherein the alcohol is a (perfluoroalkyl)ethanol or (perfluoroalkyl)propanol having three to twelve carbon atoms in the perfluoroalkyl groups; or an (omega-perfluoroisopropoxyperfluoroalkyl)ethanol or-propanol having two to ten carbon atoms in the perfluoroalkyl groups.

3. Process of claim 2 wherein the alcohol is a mixture consisting essentially of 2-(n-perfluoroalkyl)ethanols having six to twelve carbon atoms in the perfluoroalkyl groups.

4. Process of claim 3 wherein the compound esterified is pyromellitic dianhydride.

5. In a process for esterification in solution of pyromellitic anhydride with a fluorinated alcohol to form a reaction mixture containing a diester of pyromellitic acid and reaction with an oxirane compound of the group consisting of ethylene oxide, epichlorohydrin and glycidol to esterify the remaining carboxyl groups with the epoxide groups, the improvement which comprises employing a solvent for both steps consisting essentially of at least one saturated aliphatic ester having a boiling point between about 50° C. and about 150° C.

6. Process of claim 1 or 5 wherein the solvent is ethyl acetate.

7. Process of claim 1 or 5 wherein the solvent is butyl acetate.

8. Process of claim 5 wherein the product is recovered by evaporating the solvent from the product of the reaction with the epoxide groups.

9. Process of claim 8 wherein the oxirane compound is epichlorohydrin and unreacted epichlorohydrin is evaporated with the solvent.

* * * * *